(12) United States Patent
Mao et al.

(10) Patent No.: US 9,737,492 B2
(45) Date of Patent: Aug. 22, 2017

(54) CASEIN COATED DRUG-LOADED IRON OXIDE NANOPARTICLES

(71) Applicant: EMORY UNIVERSITY, Atlanta, GA (US)

(72) Inventors: Hui Mao, Johns Creek, GA (US); Jing Huang, Decatur, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 14/882,482

(22) Filed: Oct. 14, 2015

(65) Prior Publication Data

US 2016/0106684 A1 Apr. 21, 2016

Related U.S. Application Data

(60) Provisional application No. 62/064,231, filed on Oct. 15, 2014.

(51) Int. Cl.
*B82Y 5/00* (2011.01)
*A61K 9/51* (2006.01)
*A61K 31/704* (2006.01)

(52) U.S. Cl.
CPC .......... *A61K 9/5169* (2013.01); *A61K 9/5115* (2013.01); *A61K 9/5138* (2013.01); *A61K 31/704* (2013.01); *B82Y 5/00* (2013.01)

(58) Field of Classification Search
CPC ..................................................... B82Y 5/00
See application file for complete search history.

(56) References Cited

U.S. PATENT DOCUMENTS

2009/0304599 A1 12/2009 Aimi
2011/0045092 A1 2/2011 Livney

OTHER PUBLICATIONS

Atta et al. Crosslinked Poly(octadecene-alt-maleic anhydride) Copolymers as Crude Oil Sorbers, Journal of Applied Polymer Science, vol. 105, 2113-2120 (2007).
Bu et al. Assessment and comparison of magnetic nanoparticles as MRI contrast agents in a rodent model of human hepatocellular carcinoma, Contrast Media Mol Imaging. 2012; 7(4): 363-372.
Chen et al. Triblock copolymer coated iron oxide nanoparticle conjugate for tumor integrin targeting, Biomaterials 30 (2009) 6912-6919.
Duan et al. Reexamining the Effects of Particle Size and Surface Chemistry on the Magnetic Properties of Iron Oxide Nanocrystals: New Insights into Spin Disorder and Proton Relaxivity, Physical Chemistry Letters, 2008, 112, 8127-8131.
(Continued)

*Primary Examiner* — Carlos Azpuru
(74) *Attorney, Agent, or Firm* — Emory Patent Group

(57) ABSTRACT

This disclosure relates to nanoparticle drug delivery systems composed of casein (CN) coated nanoparticles, e.g., iron oxide nanoparticles coated with an inner layer and an out layer comprising the milk protein casein. In certain embodiments, drug molecules are incorporated into an inner polymeric layer coating the nanoparticles, which are subsequently coated with a casein containing outer layer, i.e., a layer-by-layer (LBL) construction. Oral administration of these casein coated nanoparticles are contemplated as experiments indicated sufficiently stability in conditions that simulate the conditions of the gut. Drugs that were loaded into the nanoparticle systems were released when the casein outer layer was gradually degraded in the presence of an intestinal protease meant to simulate conditions of the intestine.

6 Claims, 12 Drawing Sheets

(56) References Cited

OTHER PUBLICATIONS

Huang et al. Casein-Coated Iron Oxide Nanoparticles for High MRI Contrast Enhancement and Efficient Cell Targeting, ACS Appl. Mater. Interfaces 2013, 5, 4632-4639.
Lundin et al. Adsorption of lysozyme, beta-casein and their layer-by-layer formation on hydrophilic surfaces: Effect of Ionic strength, Colloids and Surfaces B: Biointerfaces 77 (2010) 1-11.
Ocean Nanotech, Iron Oxide Nanoparticles with Carboxylic Acid Group (Catalog # SHP) 2009.
Paukkonen, Casein-poly(acrylic acid) nanoparticles as controlled delivery vehicles, Master's Thesis, University of Helsinki, 2013.
Szyk-Warszynska et al. Characterization of casein and poly-L-arginine multilayer films, Journal of Colloid and Interface Science 423 (2014) 76-84.
Ying et al. In vitro evaluation of the cytotoxicity of iron oxide nanoparticles with different coatings and different sizes in A3 human T lymphocytes, Science of the Total Environment, 408 (2010) 4475-4481.
Zuo et al. Preparation and characterization of PEM-coated alginate microgels for controlled release of protein. Biomed Mater. Jun. 2012;7(3):035012.

CASEIN COATED DRUG-LOADED IRON OXIDE NANOPARTICLES

CROSS REFERENCE TO RELATED APPLICATIONS

This Application claims the benefit of U.S. Provisional Application No. 62/064,231 filed Oct. 15, 2014. The entirety of this application is hereby incorporated by reference for all purposes.

STATEMENT REGARDING FEDERALLY FUNDED RESEARCH

This invention was made with government support under R01CA154846-02 and U01CA151810-02 grants awarded by the NIH. The government has certain rights in the invention.

BACKGROUND

Feridex® contains iron oxide particles associated with dextran for used as a magnetic resonance imaging contrast media. Feraheme™ (ferumoxytol) is an anemia drug that contains iron oxide particles surrounded by a polyglucose sorbitol carboxymethylether coating. Both Feridex® and Feraheme™ are intravenous formulations.

Oral delivery is considered an ideal drug administration route because it not only avoids the discomfort and additional procedures associated with intravenous delivery injections but also allows for delivery of non-water-soluble drugs. However, oral delivery through organs in the gastrointestinal (GI) tract needs to overcome several obstacles, including: 1) the strong acidic gastric environment that reduces the drug stability and solubility; 2) the digestive enzymes that degrade drugs and decrease drug bioavailability; and 3) a mucus barrier that blocks drug penetration and subsequent tissue absorption. Even if a drug can be formulated for oral administration, it remains a challenge to deliver the drugs to a specific segment of the GI tract, such as the intestine, for maximal drug action. In clinical practice, certain drugs, for example, those for treating Crohn's disease, ulcerative colitis and chemotherapy medications, may need controlled release of the drug in the targeted areas or organs of the GI tract to increase the bioavailability and efficacy of the drug while reducing the toxicity to the normal organs and tissue. Thus there is a need to identify improved oral formulations.

Casein (CN) is a major protein ingredient in milk and can form micelle-like porous structures with the capacity of absorbing vitamins and minerals, for nutrient delivery. Huang et al. report casein-coated iron oxide nanoparticles for high MRI contrast enhancement and efficient cell targeting. ACS Appl Mater Interfaces, 5 (2013), pp. 4632-4639.

Ying et al. report the evaluation of the cytotoxicity of iron oxide nanoparticles with different coatings and different sizes. Science of the Total Environment, 408 (2010) 4475-4481.

Zuo et al. report PEM-coated alginate microgels for controlled release of protein. Biomed Mater, 7 (2012)

References cited herein are not an admission of prior art.

SUMMARY

This disclosure relates to nanoparticle drug delivery systems composed of casein (CN) coated nanoparticles, e.g., iron oxide nanoparticles coated with an inner layer and an out layer comprising the milk protein casein. In certain embodiments, drug molecules are incorporated into an inner polymeric layer coating the nanoparticles, which are subsequently coated with a casein containing outer layer, i.e., a layer-by-layer (LBL) construction. Oral administration of these casein coated nanoparticles are contemplated as experiments indicated sufficiently stability in conditions that simulate the conditions of the gut. Drugs that were loaded into the nanoparticle systems were released when the casein outer layer was gradually degraded in the presence of an intestinal protease meant to simulate conditions of the intestine.

In certain embodiments, the disclosure relates to pharmaceutical compositions comprising a particle; an inner coating on the particle comprising an amphiphilic polymer providing a hydrophobic space for embedding a hydrophobic drug within the inner coating, wherein a hydrophobic drug is in the space of the inner coating; and an outer coating over inner coating wherein the outer coating is crosslink casein molecules that are hydrophilic, making the whole nanoparticles water soluble.

In certain embodiments, the disclosure relates to methods of treating a disease or condition comprising administering an effective amount of a pharmaceutical composition of disclosed herein to a subject in need thereof. In certain embodiments, the disease is cancer and the hydrophobic drug is an anticancer drug.

DETAILED DISCUSSION

Figure 1:
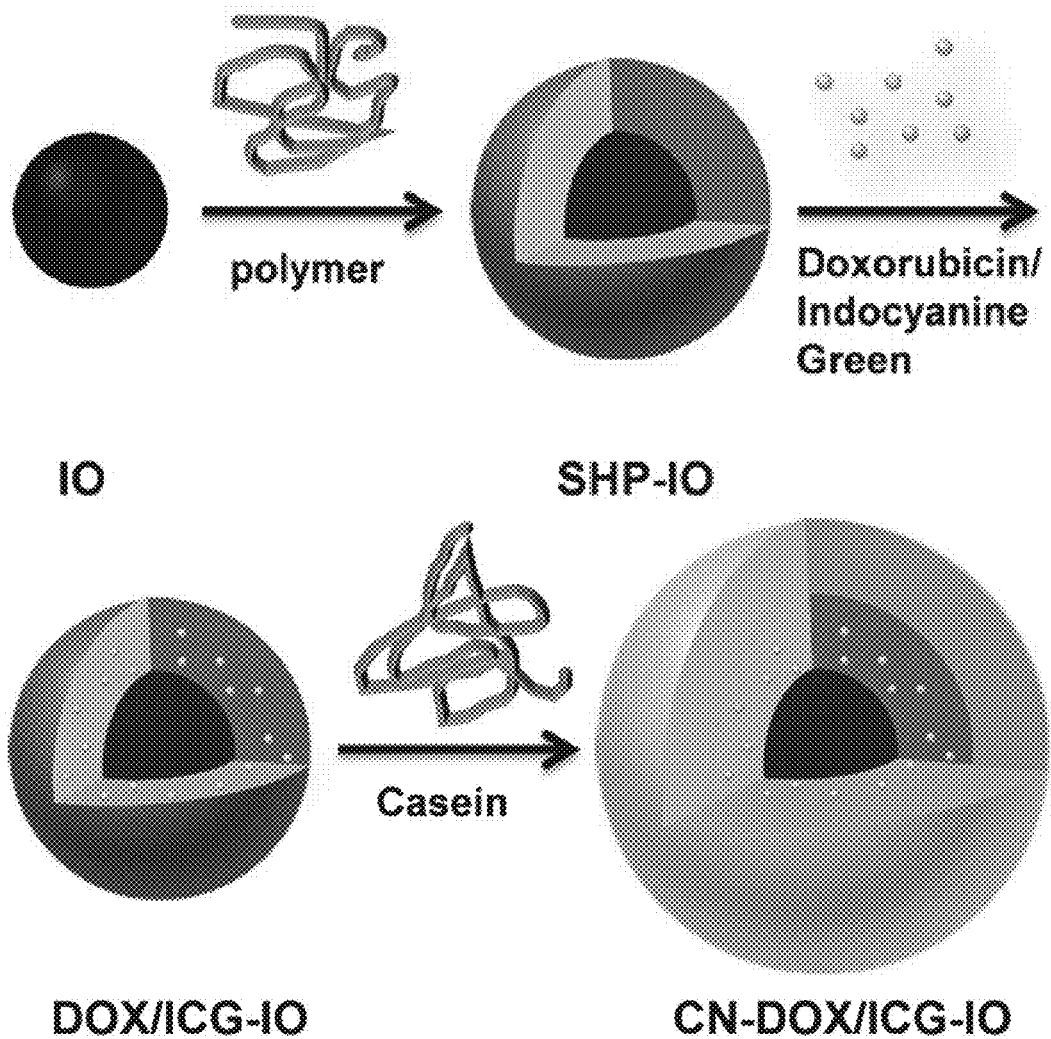
FIG. 1 shows a scheme that illustrates layer-by-layer assembly of casein coated iron oxide nanoparticles loaded with a drug (Doxorubicin/Indocyanine green).

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

Prior to describing the various embodiments, the following definitions are provided and should be used unless otherwise indicated.

As used herein, "casein" refers to a group of casein proteins ($\alpha$s1, $\beta$, $\alpha$s2 and $\kappa$) found in milk as the major components, which are coded by the genes (CSN1S1, CSN2, CSN1S2 and CSN3, respectively). The dominant feature of milk is the casein micelle, a supramolecular aggregate imparts the white characteristic of milk. Because $\alpha$s1,2-caseins and $\beta$-caseins are highly phosphorylated, they are believed to bind with calcium to form the aggregates. $\kappa$-casein is thought to predominate on the micellar surface. Casein may be purified from milk. Casein exists in milk as the calcium salt, calcium caseinate. Calcium caseinate has its isoelectric point at pH lower than the pH of milk; therefore the casein micelle is solubilized. If acid is added to milk, the casein precipitates. Further extraction with ethanol allows for further purification. Experiments performed herein utilize casein from bovine milk. In certain embodiments, the disclosure contemplates that casein is derived from other animals such as humans, buffaloes, goats, camels and sheep. In certain embodiments, the disclosure contemplates that the casein proteins may be produced by recombinant methods.

In certain embodiments, the disclosure contemplates pharmaceutical compositions comprising casein containing particles disclosed herein and a pharmaceutically acceptable excipient typically in the form of a pill, hard or soft shell capsule, tablet, gel, oral powder, or liquid formulation. Liquid and solid preparations for oral use may contain suitable antimicrobial preservatives, antioxidants and other excipients such as dispersing, suspending, thickening, emulsifying, buffering, wetting, solubilizing, stabilizing, flavoring and sweetening agents. Liquid vehicle may include sucrose or a suitable polyhydric alcohol or alcohols and which optionally contain ethanol, an elixir or linctus.

Examples of excipients include polysaccharides, petrolatum, gelatin, and mineral oil, antiadherents, binders, coatings, colors, disintegrants, flavors, glidants, lubricants, preservatives, sorbents, and sweeteners. Typical binders include saccharides, disaccharides: sucrose, lactose; polysaccharides starches, cellulose or modified cellulose such as microcrystalline cellulose and cellulose ethers such as hydroxypropyl cellulose (HPC); xylitol, sorbitol or maltitol; gelatin; polyvinylpyrrolidone (PVP), polyethylene glycol (PEG). Solution binders include gelatin, cellulose, cellulose derivatives, polyvinylpyrrolidone, starch, sucrose and polyethylene glycol. Dry binders include cellulose, methyl cellulose, polyvinylpyrrolidone and polyethylene glycol. Typical sweeteners include a saccharide like citric acid and sodium citrate. Typical preservatives include antioxidants like vitamin A, vitamin E, vitamin C, retinyl palmitate, and selenium, or amino acids like cysteine and methionine and methyl paraben and propyl paraben. Typical lubricants include talc or silica, and fats, e.g. vegetable stearin, magnesium stearate or stearic acid. Typical glidants include fumed silica, talc, and magnesium carbonate. Typical disintegrants include crosslinked polyvinylpyrrolidone (crospovidone), crosslinked sodium carboxymethyl cellulose (croscarmellose sodium) and sodium starch glycolate. Typical coatings include a cellulose ether hydroxypropyl methylcellulose (HPMC), shellac, gelatin, or polysaccharides.

"Cancer" refers any of various cellular diseases with malignant neoplasms characterized by the proliferation of cells. It is not intended that the diseased cells must actually invade surrounding tissue and metastasize to new body sites. Cancer can involve any tissue of the body and have many different forms in each body area. Within the context of certain embodiments, whether "cancer is reduced" may be identified by a variety of diagnostic manners known to one skill in the art including, but not limited to, observation the reduction in size or number of tumor masses or if an increase of apoptosis of cancer cells observed, e.g., if more than a 5% increase in apoptosis of cancer cells is observed for a sample compound compared to a control without the compound. It may also be identified by a change in relevant biomarker or gene expression profile, such as PSA for prostate cancer, HER2 for breast cancer, or others.

The cancer to be treated in the context of the present disclosure may be any type of cancer or tumor. These tumors or cancer include, and are not limited to, tumors of the hematopoietic and lymphoid tissues or hematopoietic and lymphoid malignancies, tumors that affect the blood, bone marrow, lymph, and lymphatic system. Hematological malignancies may derive from either of the two major blood cell lineages: myeloid and lymphoid cell lines. The myeloid cell line normally produces granulocytes, erythrocytes, thrombocytes, macrophages and mast cells; the lymphoid cell line produces B, T, NK and plasma cells. Lymphomas, lymphocytic leukemias, and myeloma are from the lymphoid line, while acute and chronic myelogenous leukemia, myelodysplastic syndromes and myeloproliferative diseases are myeloid in origin.

Also contemplated are malignancies located in the colon, abdomen, bone, breast, digestive system, liver, pancreas, peritoneum, endocrine glands (adrenal, parathyroid, hypophysis, testicles, ovaries, thymus, thyroid), eye, head and neck, nervous system (central and peripheral), lymphatic system, pelvis, skin, soft tissue, spleen, thorax and genitourinary apparatus and, more particularly, childhood acute lymphoblastic leukemia, acute lymphoblastic leukemia, acute lymphocytic leukemia, acute myeloid leukemia, adrenocortical carcinoma, adult (primary) hepatocellular cancer, adult (primary) liver cancer, adult acute lymphocytic leukemia, adult acute myeloid leukemia, adult Hodgkin's disease, adult Hodgkin's lymphoma, adult lymphocytic leukemia, adult non-Hodgkin's lymphoma, adult primary liver cancer, adult soft tissue sarcoma, AIDS-related lymphoma, AIDS-related malignant tumors, anal cancer, astrocytoma, cancer of the biliary tract, cancer of the bladder, bone cancer, brain stem glioma, brain tumors, breast cancer, cancer of the renal pelvis and ureter, primary central nervous system lymphoma, central nervous system lymphoma, cerebellar astrocytoma, brain astrocytoma, cancer of the cervix, childhood (primary) hepatocellular cancer, childhood (primary) liver cancer, childhood acute lymphoblastic leukemia, childhood acute myeloid leukemia, childhood brain stem glioma, childhood cerebellar astrocytoma, childhood brain astrocytoma, childhood extracranial germ cell tumors, childhood Hodgkin's disease, childhood Hodgkin's lymphoma, childhood visual pathway and hypothalamic glioma, childhood lymphoblastic leukemia, childhood medulloblastoma, childhood non-Hodgkin's lymphoma, childhood supratentorial primitive neuroectodermal and pineal tumors, childhood primary liver cancer, childhood rhabdomyosarcoma, childhood soft tissue sarcoma, childhood visual pathway and hypothalamic glioma, chronic lymphocytic leukemia, chronic myeloid leukemia, cancer of the colon, cutaneous T-cell lymphoma, endocrine pancreatic islet cells carcinoma, endometrial cancer, ependymoma, epithelial cancer, cancer of the oesophagus, Ewing's sarcoma and related tumors, cancer of the exocrine pancreas, extracranial germ cell tumor, extragonadal germ cell tumor, extrahepatic biliary tract cancer, cancer of the eye, breast cancer in women, Gaucher's disease, cancer of the gallbladder, gastric cancer, gastrointestinal carcinoid tumor, gastrointestinal tumors, germ cell tumors, gestational trophoblastic tumor, tricoleukemia, head and neck cancer, hepatocellular cancer, Hodgkin's disease, Hodgkin's lymphoma, hypergammaglobulinemia, hypopharyngeal cancer, intestinal cancers, intraocular melanoma, islet cell carcinoma, islet cell pancreatic cancer, Kaposi's sarcoma, cancer of kidney, cancer of the larynx, cancer of the lip and mouth, cancer of the liver, cancer of the lung, lymphoproliferative disorders, macroglobulinemia, breast cancer in men, malignant mesothelioma, malignant thymoma, medulloblastoma, melanoma, mesothelioma, occult primary metastatic squamous neck cancer, primary metastatic squamous neck cancer, metastatic squamous neck cancer, multiple myeloma, multiple myeloma/plasmatic cell neoplasia, myelodysplastic syndrome, myelogenous leukemia, myeloid leukemia, myeloproliferative disorders, paranasal sinus and nasal cavity cancer, nasopharyngeal cancer, neuroblastoma, non-Hodgkin's lymphoma during pregnancy, non-melanoma skin cancer, non-small cell lung cancer, metastatic squamous neck cancer with occult primary, buccopharyngeal cancer, malignant fibrous histiocytoma, malignant fibrous osteosarcoma/histiocytoma of the bone, epithelial ovarian cancer, ovarian germ cell tumor, ovarian low malignant potential tumor, pancreatic cancer, paraproteinemias, purpura, parathyroid cancer, cancer of the penis, phaeochromocytoma, hypophysis tumor, neoplasia of plasmatic cells/multiple myeloma, primary central nervous system lymphoma, primary liver cancer, prostate cancer, rectal cancer, renal cell cancer, cancer of the renal pelvis and ureter, retinoblastoma, rhabdomyosarcoma, cancer of the salivary glands, sarcoidosis, sarcomas, skin cancer, small cell lung cancer, small intestine cancer, soft tissue sarcoma, squamous neck cancer, stomach cancer, pineal and supratentorial primitive neuroectodermal tumors, T-cell lymphoma, testicular cancer, thymoma, thyroid cancer, transitional cell cancer of the renal pelvis and ureter, transitional renal pelvis and ureter cancer, trophoblastic tumors, cell cancer of the renal pelvis and ureter, cancer of the urethra, cancer of the uterus, uterine sarcoma, vaginal cancer, optic pathway and hypothalamic glioma, cancer of the vulva, Waldenstrom's macroglobulinemia, Wilms' tumor and any other hyperproliferative disease, as well as neoplasia, located in the system of a previously mentioned organ.

A "chemotherapy agent," "chemotherapeutic," "anti-cancer agent" or the like, refer to molecules that are recognized to aid in the treatment of a cancer. Contemplated examples include the following molecules or derivatives such as temozolomide, carmustine, bevacizumab, procarbazine, lomustine, vincristine, gefitinib, erlotinib, cisplatin, carboplatin, oxaliplatin, 5-fluorouracil, gemcitabine, tegafur, raltitrexed, methotrexate, cytosine arabinoside, hydroxyurea, adriamycin, bleomycin, doxorubicin, daunomycin, epirubicin, idarubicin, mitomycin-C, dactinomycin, mithramycin, vinblastine, vindesine, vinorelbine, paclitaxel, taxol, docetaxel, etoposide, teniposide, amsacrine, topotecan, camptothecin, bortezomib, anagrelide, tamoxifen, toremifene, raloxifene, droloxifene, iodoxyfene, fulvestrant, bicalutamide, flutamide, nilutamide, cyproterone, goserelin, leuprorelin, buserelin, megestrol, anastrozole, letrozole, vorozole, exemestane, finasteride, marimastat, trastuzumab, cetuximab, dasatinib, imatinib, combretastatin, thalidomide, azacitidine, azathioprine, capecitabine, chlorambucil, cyclophosphamide, cytarabine, daunorubicin, doxifluridine, epothilone, irinotecan, mechlorethamine, mercaptopurine, mitoxantrone, pemetrexed, tioguanine, valrubicin and/or lenalidomide or combinations thereof such as cyclophosphamide, methotrexate, 5-fluorouracil (CMF); doxorubicin, cyclophosphamide (AC); mustine, vincristine, procarbazine, prednisolone (MOPP); sdriamycin, bleomycin, vinblastine, dacarbazine (ABVD); cyclophosphamide, doxorubicin, vincristine, prednisolone (CHOP); bleomycin, etoposide, cisplatin (BEP); epirubicin, cisplatin, 5-fluorouracil (ECF); epirubicin, cisplatin, capecitabine (ECX); methotrexate, vincristine, doxorubicin, cisplatin (MVAC).

As used herein, the term "combination with" when used to describe administration with an additional treatment means that the agent may be administered prior to, together with, or after the additional treatment, or a combination thereof.

As used herein, "subject" refers to any animal, preferably a human patient, livestock, or domestic pet.

As used herein, the terms "prevent" and "preventing" include the prevention of the recurrence, spread or onset. It is not intended that the present disclosure be limited to complete prevention. In some embodiments, the onset is delayed, or the severity is reduced.

As used herein, the terms "treat" and "treating" are not limited to the case where the subject (e.g. patient) is cured and the disease is eradicated. Rather, embodiments of the present disclosure also contemplate treatment that merely reduces symptoms, and/or delays disease progression.

Casein Protein Coated Magnetic Nanoparticle Enabled Oral Drug Delivery

This disclosure relates to nanoparticle drug delivery systems composed of casein (CN) coated nanoparticles, e.g., iron oxide nanoparticles coated with an inner layer and an out layer comprising the milk protein casein. In certain embodiments, drug molecules are incorporated into an inner polymeric layer coating the nanoparticles, which are subsequently coated with a casein containing outer layer, i.e., a layer-by-layer (LBL) construction. Oral administration of these casein coated nanoparticles are contemplated as experiments indicated sufficiently stability in conditions that simulate the conditions of the gut. Drugs that were loaded into the nanoparticle systems were released when the casein outer layer was gradually degraded in the presence of an intestinal protease meant to simulate conditions of the intestine.

A pH stable and enzymatic-responsive oral drug delivery nanoparticle system with MRI visible contrast has been developed via a layer-by-layer design, using modified milk protein casein to form an outer layer that protected the hydrophobic drug loaded in the inner polymer coating layer which caps the magnetic iron oxide nanoparticle core. The casein outer layer is resistant to degradation by protease pepsin at low pH under gastric conditions, and can be disassembled by the small intestine enzyme trypsin at neutral pH. Therefore, small intestine targeted drug delivery can be achieved by reducing the pre-mature drug release in the acidic stomach and then conducting the enzymatic-responsive release in the small intestine. Furthermore, this nanoconstruct retains the ability to provide an effective MRI contrast enhancing effect, providing the potential capability of MRI monitored and/or magnetic directed drug delivery. Given high water solubility, pH stability and enzymatic responsiveness as well as excellent biocompatibility, the reported LBL CN-DOX-IO is a promising drug delivery system for oral delivery of hydrophobic drugs, capable of by-passing low stomach pH and enabling absorption in the lower GI tract with neutral pH.

The structured nanocarriers presented herein provide an approach for preferential drug delivery to the intestine, with good stability in the low pH stomach fluid and enhanced mucosal/membrane penetration, mainly attributed to the casein coating of the nanostructure. Most layered structures are microsized or have positive surface charge, which are unstable in the acidic stomach, thus not suitable for the intestinal-specific drug delivery. Experiments herein indicate that, the LBL CN-DOX-IO nanoparticles show a significant reduction of the initial rapid release of DOX from the amphiphilic inner polymer layer in the low pH conditions of the stomach fluid. Therefore, a higher amount of payload drug was retained for delivery and release in the intestine.

In addition to the protective function of the outer casein layer, casein enhances the cellular uptake. Significant enhanced permeability of LBL CN-DOX-IO was observed in the ex vivo experiment using small intestine sacs treated with different nanoconstructs, in which we observed more LBL CN-DOX-IO delivered deeply into the villi pits compared to DOX-IO without the casein outer layer. Although the mechanism by which casein improved the cell uptake and tissue penetration remained unclear and it is not intended the embodiments of this disclosure be limited by any particular mechanism, the LBL CN-DOX-IO likely has the ability to penetrate the mucus, which is one of the major obstacles for intestinal drug delivery. This enhanced absorption in intestinal villi was further confirmed by the histological analysis with Prussian blue staining. Blue dots stained by iron could be observed in the intestinal villi 3 h after oral administration of the LBL construct, but not in those treated with DOX-IO.

In vivo monitoring of drug delivery with non-invasive imaging has become a desirable tool for planning and evaluating the therapeutic strategy as well as optimizing individualized treatments. Most development and investigation of the intestinal drug delivery systems are dependent on the in vitro assessment/evaluation with conventional methods, such as cellular uptake and mucus penetration. Drug delivery systems combined with imaging probes for imaging strategies, such as QDs, radioactive moieties and NIR dyes, have recently been developed for image-guided assessment. Magnetic nanoparticles act as a core for the LBL structure, which provides a template for the LBL assembly and offers MRI contrast enhancement. As a result, the LBL nanoconstruct is useful for MRI monitoring drug delivery. Furthermore, magnetic iron oxide nanoparticles present potential capabilities of thermal-induced drug release and magnetic localization to improve the drug delivery with the reported LBL drug delivery system.

In certain embodiments, magnetic iron oxide nanoparticle cores can be used as an MRI contrast agent for in vivo imaging and guided drug delivery. Thus in certain embodiments, the disclosure contemplates methods of imaging comprising administering drug delivery systems disclosed herein to a subject in need thereof and exposing an area of the subject, e.g. an area of suspected cancer growth such as a tissue, organ, or the circulatory system, to an induced magnetic field under conditions such that magnetic resonance can detect the core of the iron oxide nanoparticle at a location and generating an image that identifies the location of the core in relation to other surrounding cells, tissues, organs, liquids, or bones.

In certain embodiments, the disclosure contemplates generating sufficiently localized heat or hypothermia in an area or location of the imaged coated iron oxide nanoparticles to cause cell wall or tissue breakdown or destruction.

The utilization of DOX and ICG were to model drug molecules. Hydrophobic drugs to specific diseases can be applied with the reported LBL construct.

In certain embodiments, the nanoparticle systems may be targeted to cells, tissues, organs, or bones by covalent attachment of a specific binding agent, e.g., that binds a cell surface marker, to the outer layer.

In certain embodiments, the disclosure relates to pharmaceutical compositions comprising a particle; an inner coating on the particle comprising an amphiphilic polymer providing an space for embedding a hydrophobic drug within the inner coating, wherein a hydrophobic drug is in the space of the inner coating; and an outer coating on the inner coating wherein the outer coating is crosslink casein molecules.

In certain embodiments, the particle is an iron oxide nanoparticle. In certain embodiments, the amphiphilic polymer comprises maleic acid and octadecene monomers.

In certain embodiments, the hydrophobic drug is an anticancer drug. In certain embodiments, the anticancer drug is doxorubicin. In certain embodiments, the crosslinked casein molecules are made by the process of mixing casein and the particle comprising the inner coating in the presences of glutaraldehyde.

In certain embodiments, the disclosure relates to methods of treating a disease or condition comprising administering an effective amount of a pharmaceutical composition of disclosed herein to a subject in need thereof. In certain embodiments, the disease is cancer and the hydrophobic drug is an anticancer drug.

EXAMPLES

Magnetic Iron Oxide Nanoparticles (SHP-IO)

Iron oxide nanoparticles with a monolayer of oleic acid and an average core diameter of 10 nm are mixed with a hydrolyzed copolymer of poly(maleic acid) and octadecene to provide an amphiphilic coating. See Duan et al. J. Phys. Chem. C, 2008, 112 (22), pp 8127-8131.

Preparation of LBL Casein Coated IO Nanoparticles Loaded with Doxorubicin

The process for preparing the layer-by-layer (LBL) assembled casein coated iron oxide nanoparticles loaded with drugs (DOX/ICG) (CN-DOX/ICG-IO) is illustrated in the scheme of FIG. 1. The inner layer of amphiphilic polymer offered a coating layer for the IO nanoparticle core along with the space for embedding the hydrophobic small molecules DOX/ICG. CN was then deposited and assembled into an outer layer. SHP-IO nanoparticle suspension (1 mg/mL) was mixed with freshly prepared doxorubicin solution in methanol (1 mg/mL). The mixture was shaken and incubated for 2 h so that hydrophobic DOX could be incorporated into the hydrophobic layer of the amphiphilic coating polymer. Doxorubicin-loaded iron oxide nanoparticles (DOX-IO) were collected by centrifuging using a centrifuge tube with a cut-off size of 100 kDa. Collected DOX-IO was rinsed several times with deionized water until no free DOX was detected in the rinsing solution.

Formation of LBL CN-DOX-IO Nanoparticles

DOX-IO solution was mixed with casein (CN) solution at the weight ratio of Fe:CN=1:2. The mixture was kept at room temperature for 24 h to allow casein molecules to assemble on the surface of DOX-IO. Then a freshly prepared 0.4% glutaraldehyde solution was added to crosslink the casein molecules to form an outer layer on the surface of DOX-IO. After 2 h, the product of casein coated doxorubicin-loaded iron oxide nanoparticles (CN-DOX-IO) was collected by centrifuging using a centrifuge tube with a cut-off size of 100 kDa, and washed with deionized water three times.

The core diameters, hydrodynamic sizes and zeta potentials of the prepared DOX-IO and CN-DOX-IO were determined by transmission electron microscope (TEM, HitachiH-7500, accelerating voltage 75 kV) and dynamic light scattering (DLS, Malvern Zeta Sizer Nano S-90) instrument, respectively. Gel electrophoresis was performed to confirm the presence of casein coating in CN-DOX-IO using 2% agarose gel. The percentage of DOX loaded on IONPs was determined by the weight ratio of loaded DOX to Fe. Samples were dissolved in 1 m HCl, and sonicated for 30 min, and then measured for the fluorescence intensity from DOX at 590 nm ($\lambda_{ex}$=485 nm) with a microplate reader (Synergy 2 Multi-Mode Microplate Reader, BioTek, USA) to determine the amount of loaded DOX. The Fe concentration was determined by the phenanthroline-colorimetric method.

Figure 2A:
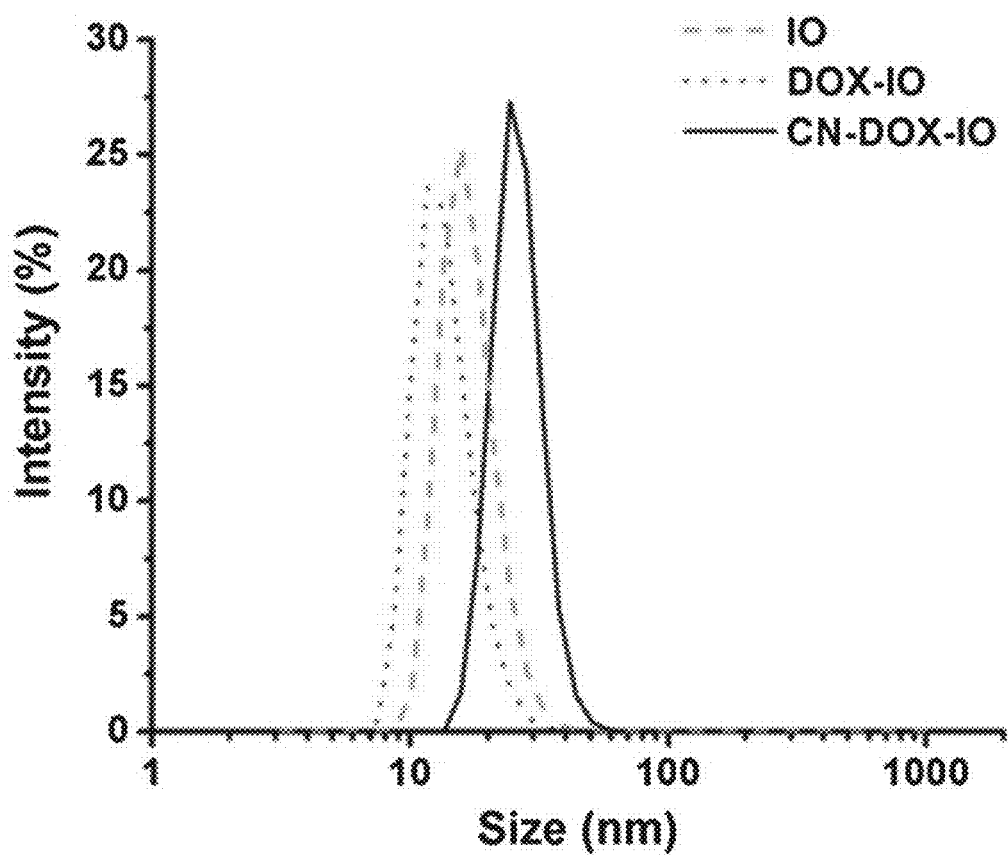
FIG. 2A shows data on DLS profiles of size distribution of SHP-IO, DOX-IO, CN-DOX-IO.
Figure 2B:
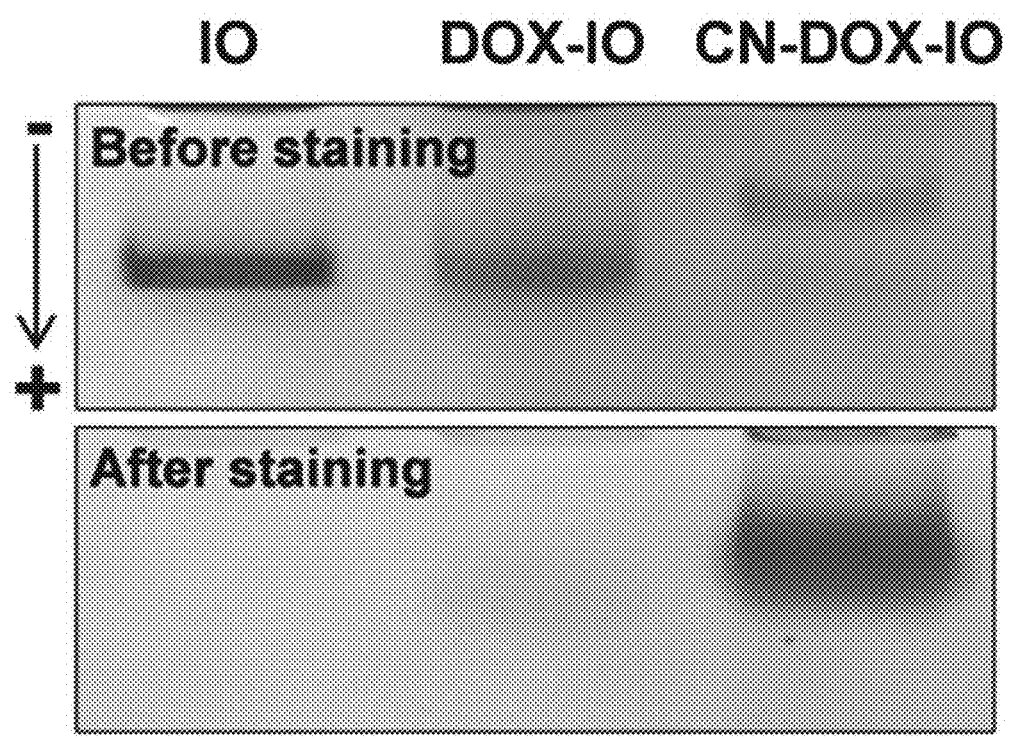
FIG. 2B shows gel electrophoresis of SHP-IO, DOX-IO, CN-DOX-IO (upper), and corresponding GelCode Blue staining for the presence of casein coating.
Figure 2C:
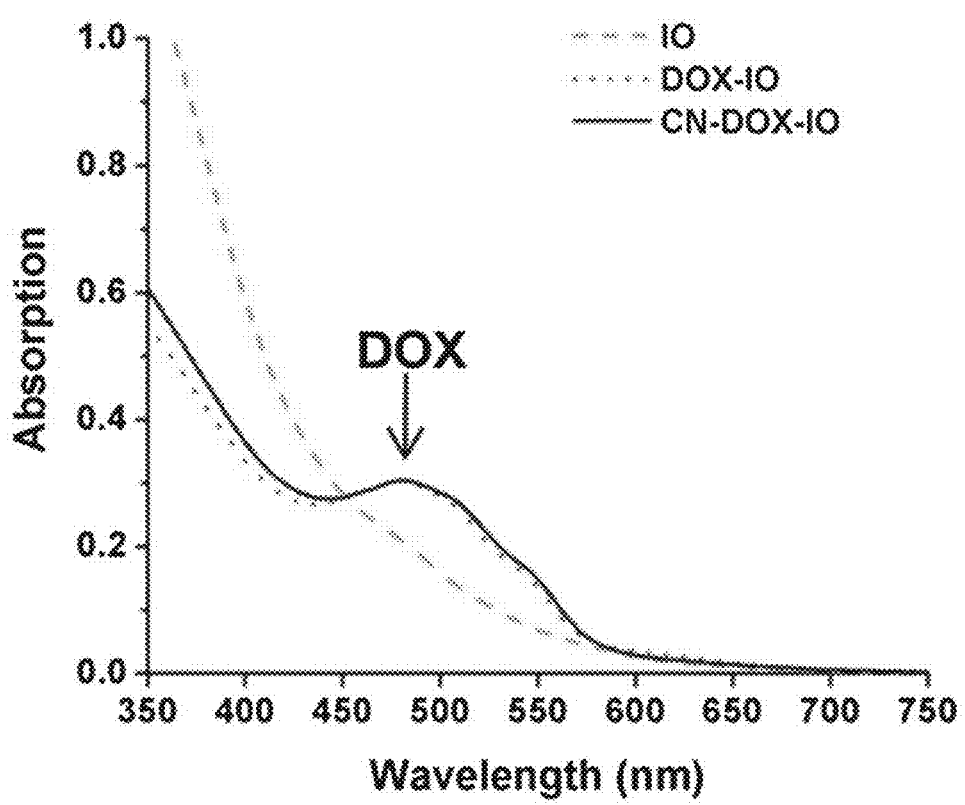
FIG. 2C shows data on UV-Vis absorption spectra of SHP-IO, DOX-IO and CN-DOX-IO with distinctive peak of DOX indicated.

From TEM images of SHP-IO, DOX-IO and LBL CN-DOX-IO nanoparticles (FIG. 1) the average diameters of the IO nanoparticle cores, measured from 100 individual nanoparticles in the TEM images, are calculated to be: 10.1±0.6, 10.4±0.5, and 10.4±0.6 for SHP-IO, DOX-IO and CN-DOX-IO, respectively. This indicates the core size of IO nanoparticles remained unchanged after DOX loading in the inner polymeric layer and subsequent assembly of the casein outer layer. The formation of LBL CN-DOX-IO was confirmed by the increased hydrodynamic sizes with increasing coating layers. After coating with amphiphilic polymer, hydrophobic IO nanoparticles were transferred into aqueous solution, and consequently the hydrodynamic size increased from 10.1 nm (IO, data not shown) to 18.8 nm (SHP-IO). However, the hydrodynamic size of DOX-IO (17.7±3.8 nm) was slightly smaller compared with that of SHP-IO, which was attributed to the contraction of the polymer coating when DOX was absorbed in the methanol/water mixture. The hydrodynamic sizes increased to 24.4±4.67 nm (CN-DOX-IO) after applying the outer layer of CN (FIG. 2A). Furthermore, gel electrophoresis demonstrated a higher molecular weight and lower mobility of LBL CN-DOX-IO comparing to that of DOX-IO and SHP-IO (FIG. 2B). It is notable that DOX-IO showed the highest mobility in electrophoresis because of its smallest size. Subsequently staining the gel with GelCode Blue evidenced a marked blue band in CN-DOX-IO, indicating the presence of protein coating on CN-DOX-IO. In contrast, no such band was observed for SHP-IO and DOX-IO (FIG. 2B). The UV-Vis absorption spectra of both DOX-IO and CN-DOX-IO revealed the characteristic peak of DOX at 495 nm, as shown in FIG. 2C, representing that DOX was successfully loaded on DOX-IO and remained in the LBL CN-DOX-IO structure when the casein outer layer formed. All three types of nanoparticles exhibited excellent water solubility and were stable in water over months of storage without aggregation/precipitation.

Figure 3A:
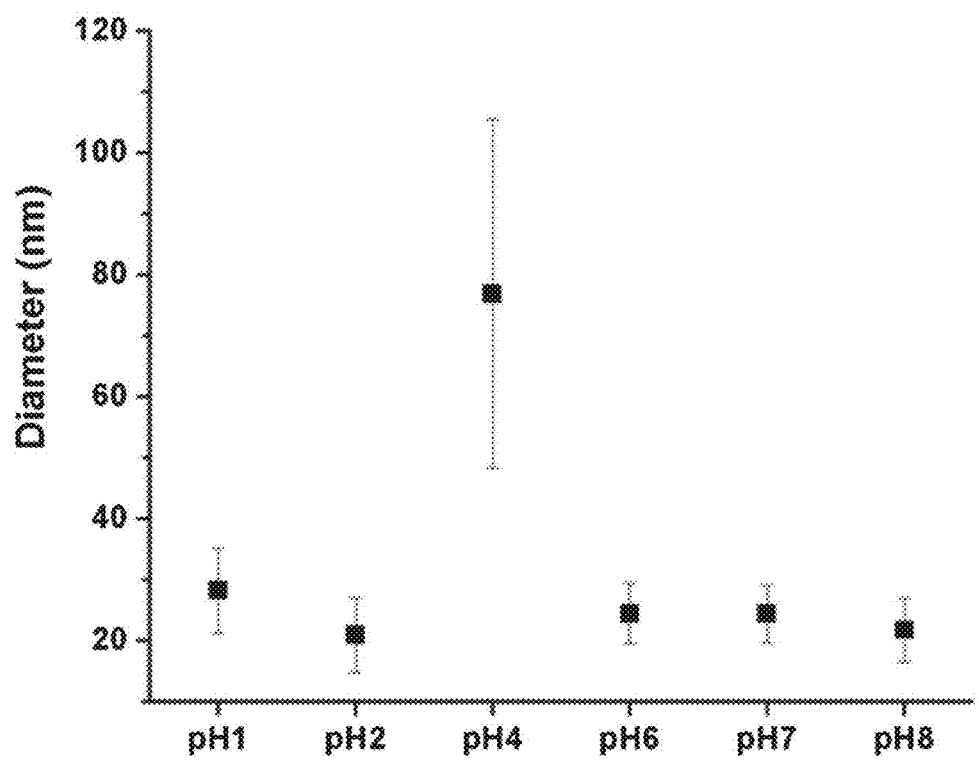
FIG. 3A shows data on the changes of the hydrodynamic size at different pH of CN-DOX-IO nanoparticles measured by DLS.
Figure 3B:
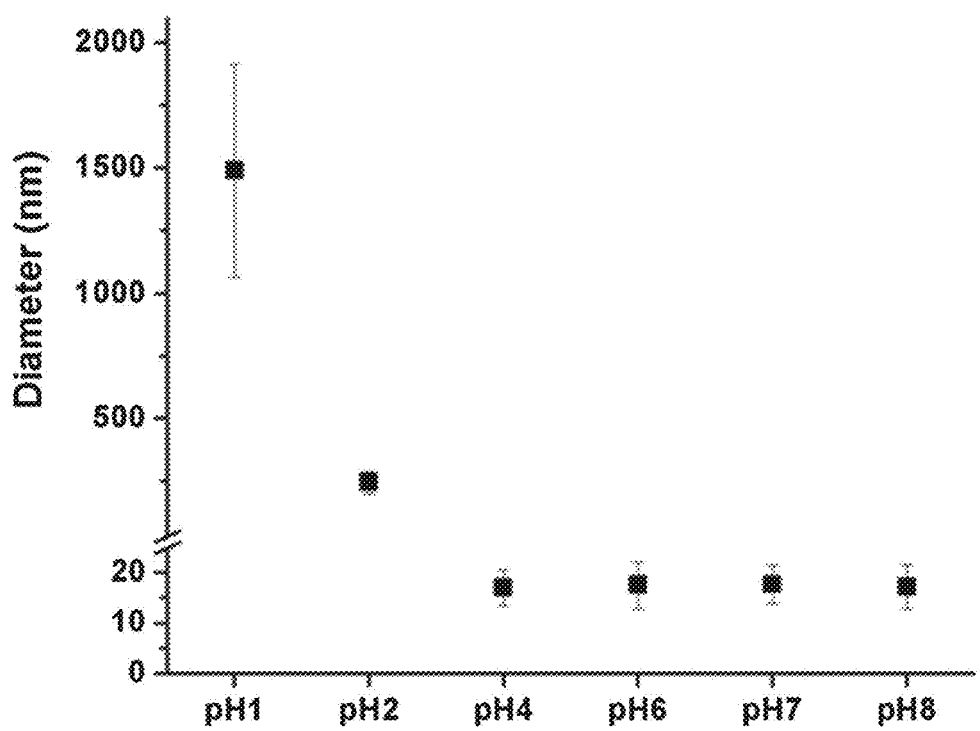
FIG. 3B shows data on the changes of the hydrodynamic size at different pH of DOX-IO nanoparticles measured by DLS.

Stabilities of CN-DOX-IO at Low pH and Against Gastric and Small Intestine Enzymes Selectively delivering drugs to the intestine requires conquering the gastric acidic and enzymatic conditions that may prematurely release, degrade and deactivate the drugs The prepared LBL CN-DOX-IO was stable over the pH range of 2.0-8.0. DLS measured hydrodynamic sizes of CN-DOX-IO (~25 nm) remained unchanged over this pH range (FIG. 3A) except at the isoelectric point of pH 4.0, in which the hydrodynamic sizes increased to 80 nm. At the isoelectric point of pH 4.0, monodispersed CN-DOX-IO formed reversible clusters, but not precipitation. This reversible aggregation returned to the single dispersed form (with hydrodynamic size of 25 nm) by adjusting pH to lower/higher than the isoelectric point, due to the presence of abundant positive/negative charged functional groups in CN. At pH 2.0, which is close to the pH condition of the stomach fluid, CN-DOX-IO remained single dispersed with a hydrodynamic size of 25 nm for more than 24 h. On the contrary, DOX-IO without the protective casein outer layer precipitated when pH changed to 2.0 and below, evidenced by the drastic increase of the hydrodynamic size (FIG. 3B).

To examine the stability of the casein outer layer in CN-DOX-IO against digestive enzymes in stomach and its enzymatic-responsive degradation by the digestive enzymes in the small intestine, CN-DOX-IO was treated with pepsin, which is the protease in the gastric juice that breaks down protein to peptides, and trypsin, which is a duodenum secreted protease that degrades protein or peptides, at different enzyme concentrations at pH 2.0 (for pepsin) and 7.0 (for trypsin). SDS-PAGE gel electrophoresis was used to examine the protein or peptides digested by the enzymes.

Figure 3C:
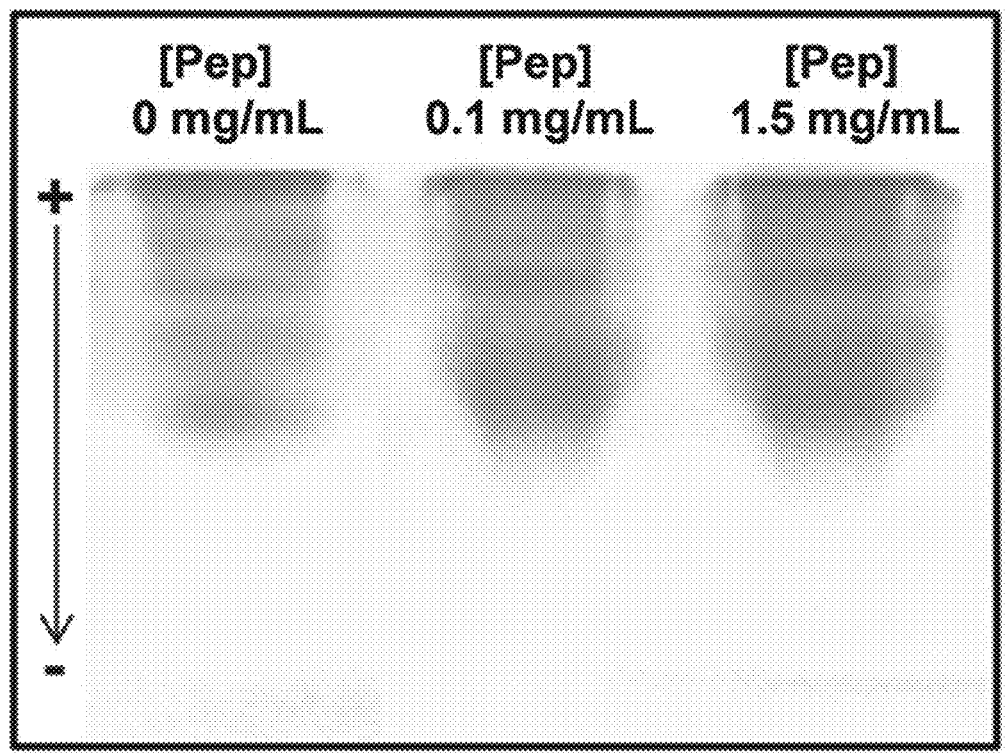
FIG. 3C shows SDS-PAGE analysis of digested protein fragments from the coating layer of CN-DOX-IO after treated with gastric enzyme pepsin at pH 2.0
Figure 3D:
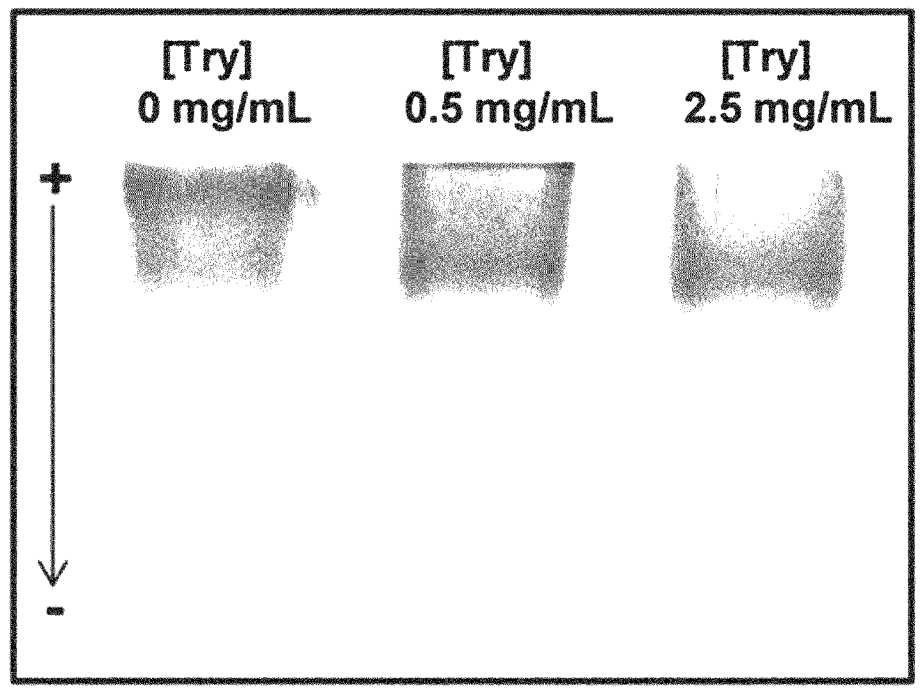
FIG. 3D shows SDS-PAGE analysis of digested protein fragments from the coating layer of CN-DOX-IO after treated with small intestine enzyme trypsin at pH 7.
Figure 3E:
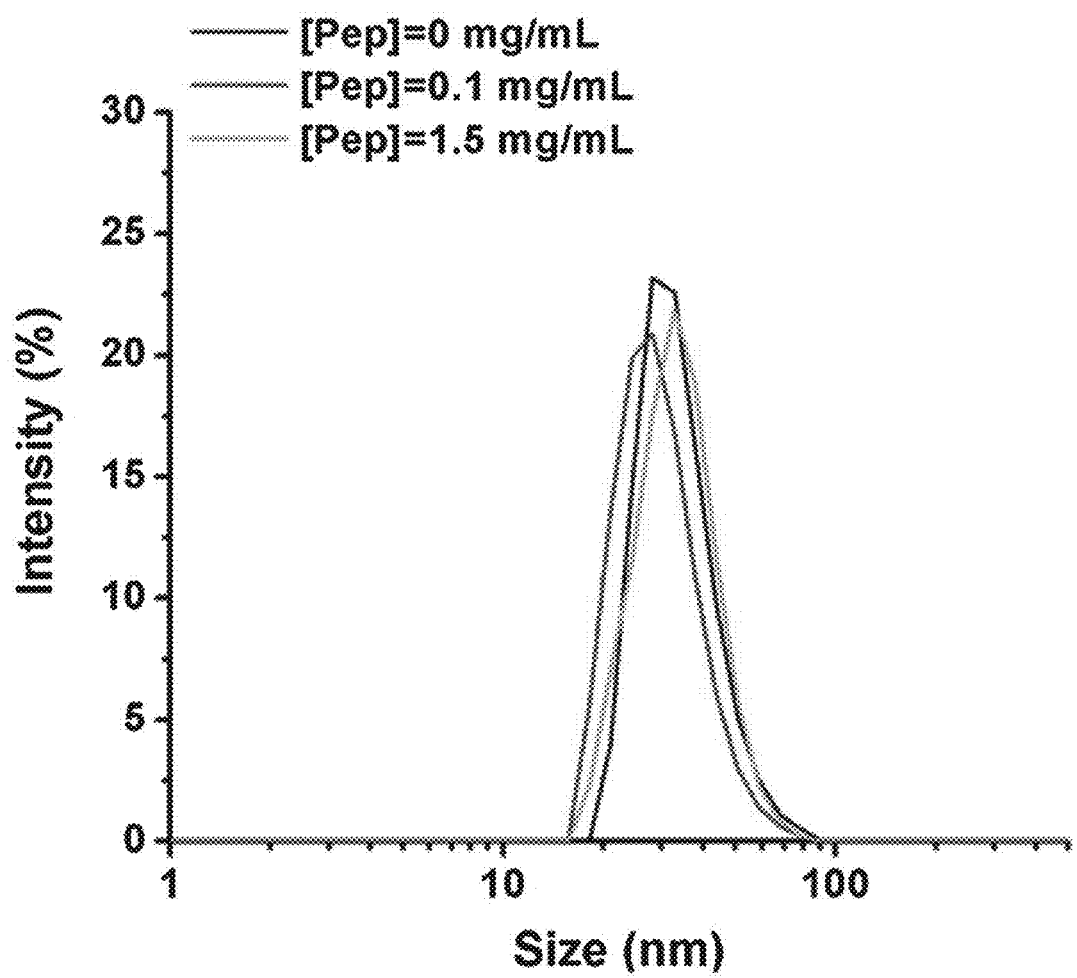
FIG. 3E shows data on changes of hydrodynamic sizes of CN-DOX-IO after treated with pepsin at pH 2.0 at different enzyme concentrations
Figure 3F:
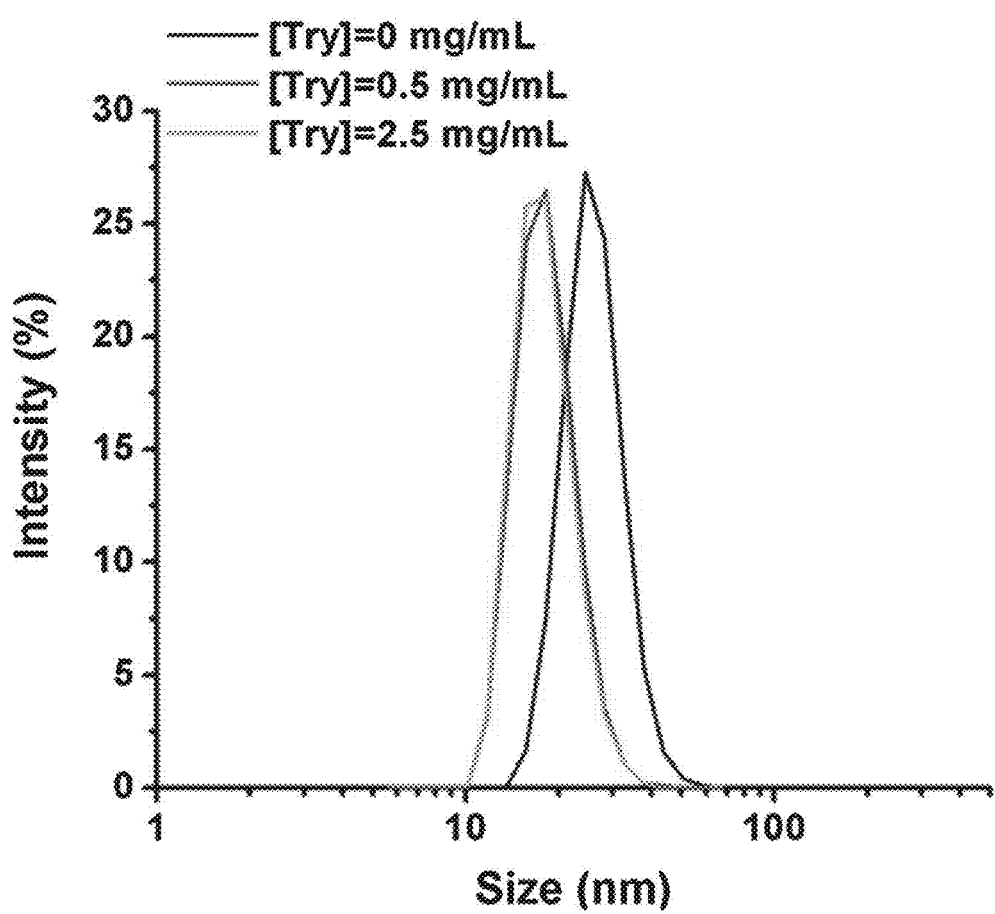
FIG. 3F shows data on changes of hydrodynamic sizes of CN-DOX-IO after treated with trypsin at pH 7.0 at different enzyme concentrations.

The band of CN in SDS-PAGE gel was still observed (FIG. 3C) after treatment at pH 2.0 with pepsin (0.1 and 1.5 mg/mL), which represented the physiological enzyme range of human gastric fluid (0.3-1.3 mg pepsin/mL). DLS measurements of CN-DOX-IO treated with pepsin at pH 2.0 also validated the stability of the reported LBL nanostructure in the mimicked gastric digestive system. CN-DOX-IO showed persistent dispersibility with unvaried hydrodynamic size after treated with pepsin (FIG. 3E). On the other hand, SDS-PAGE showed different bands when treating CN-DOX-IO with trypsin at pH 7.0 (FIG. 3D). The amount of intact CN in DOX-CN-IO decreased while short peptides and fragments of CN emerged in the SDS-PAGE gel. The size of newly appearing peptide fragments became smaller (lower molecular weight in SDS-PAGE gel) as the trypsin concentration further increased. DLS measurement showed a decrease in hydrodynamic size of CN-DOX-IO after treated with trypsin (FIG. 3F), which further confirmed the breakdown of the casein outer layer. These results indicate that LBL CN-DOX-IO nanoparticles can remain intact under the acidic gastric condition with a protective casein outer layer resistant to the low pH and pepsin. In addition, the casein outer layer can be disassembled by the intestine protease trypsin at pH 7.0, thus exposing the inner layer of amphiphilic polymer, which is loaded with the hydrophobic drug (DOX). Therefore, this LBL delivery vehicle is suitable for oral drug delivery through the GI tract to the intestine.

Enzymatic Responsive Release of Doxorubicin from CN-DOX-IO

Figure 4A:
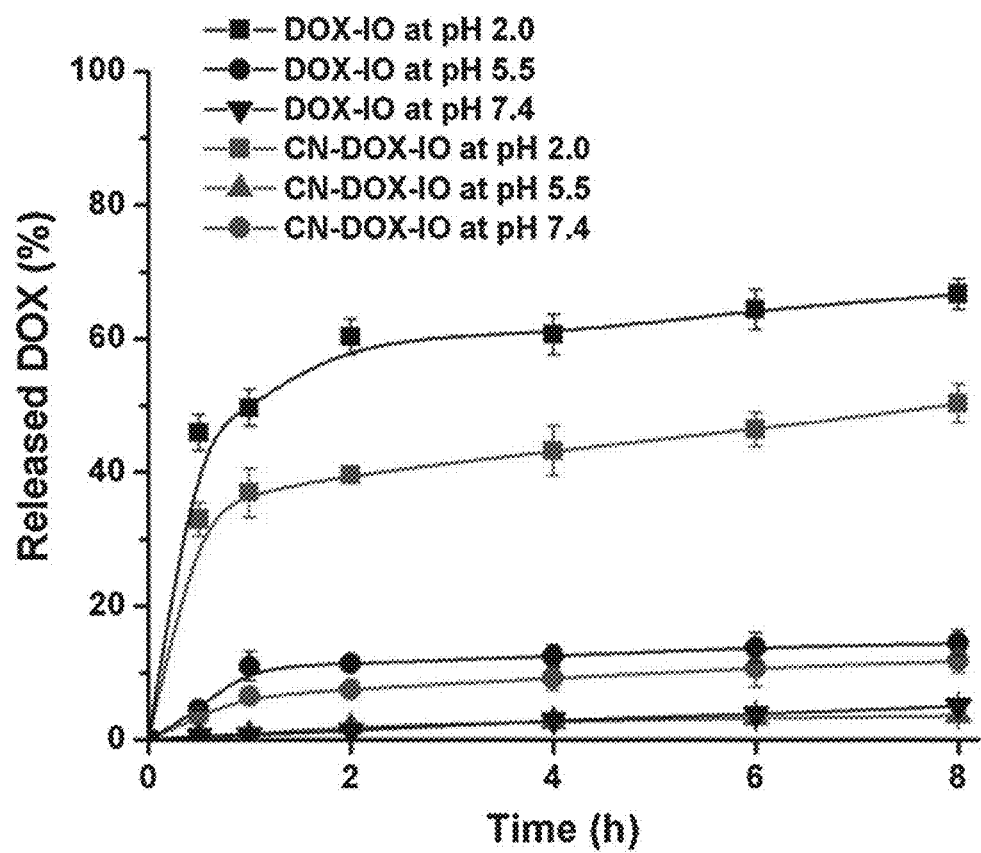
FIG. 4A shows data on release profiles of DOX from CN-DOX-IO and DOX-IO at different pH, in the simulated gastric juice (pH 2.0, [Pep]=1.0 mg/mL).
Figure 4B:
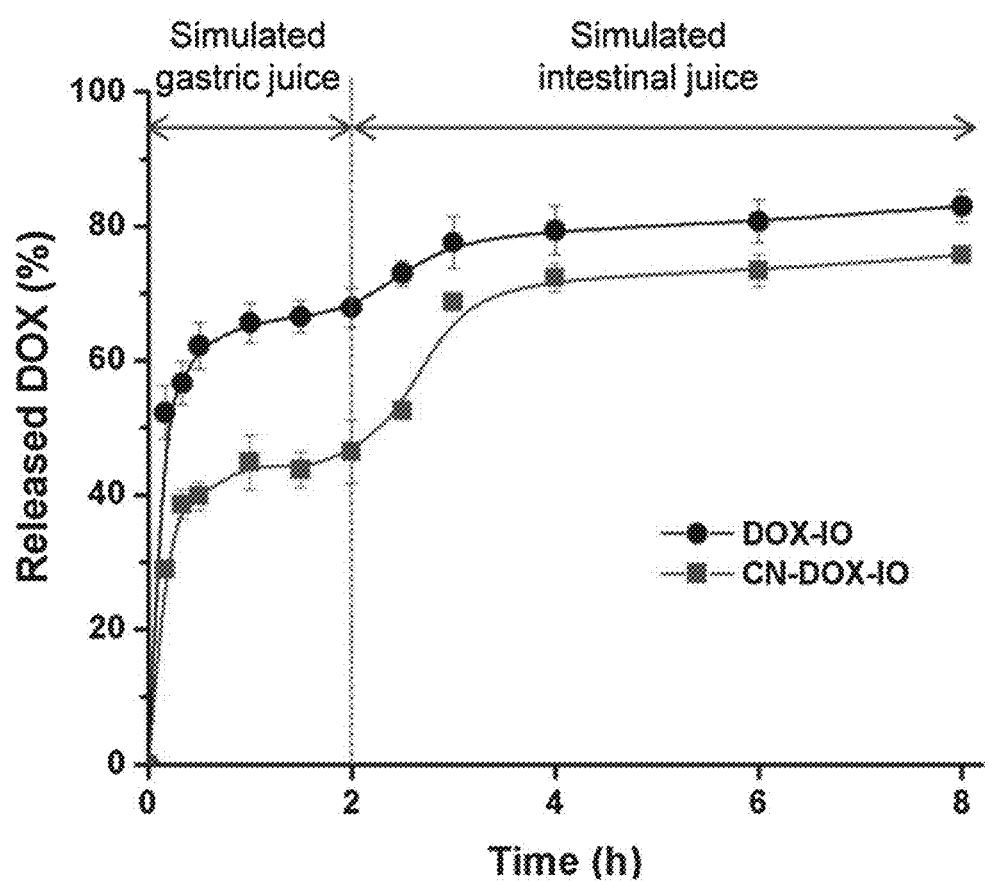
FIG. 4B shows data on release profiles of DOX from CN-DOX-IO and DOX-IO at different pH, in the simulated intestinal juice (pH 7.0, [Try]=2.5 mg/mL).

FIG. 4A shows the profiles of DOX released from the CN-DOX-IO nanoparticles and those from DOX-IO at pH 2.0, 5.5 and 7.4 without the presence of either pepsin or trypsin. Both of the DOX loaded nanoparticles exhibited very low release of DOX at pH 5.5 and 7.4, compared to that at pH 2.0. The increased release of DOX at lower pH (2.0) is caused by the protonated DOX, which has a higher solubility in water. Notably, CN-DOX-IO exhibited a slower and sustained release of DOX compared with DOX-IO at pH 2.0, referring to the effective protection of DOX by the casein outer layer. When cultured in the medium simulating gastric juice (pH 2.0, [Pep]=1.0 mg/mL), the initial rapid release of the encapsulated DOX in DOX-IO (62%) was significantly reduced to about 40% when casein outer layer was applied (FIG. 4B). The results implied that the embedded DOX in the inner amphiphilic polymer layer in DOX-IO was shielded by the pH- and pepsin-stable casein outer layer. Alternatively, both DOX-IO and CN-DOX-IO showed sustained release of DOX in the simulated intestinal juice (pH 7.0, [Try]=2.5 mg/mL). DOX was released from CN-DOX-IO more effectively (~30% in 6 h) in the medium simulating intestinal juice than from DOX-IO (~15% in 6 h). The LBL CN-DOX-IO demonstrated a preferential and enzymatic-responsive drug release property by preventing the loss of drug in the acidic stomach, thus improving the efficacy of drug delivery to the small intestine.

Uptake of CN-DOX-IO by Caco-2 Cell Monolayer

To investigate the cellular uptake of the released DOX from CN-DOX-IO by the small intestine in vitro, the monolayer of Caco-2 cells was incubated with CN-DOX-IO at a dosage of 17.2 μm for different lengths of time (10, 30 and 60 min). For comparison, cells incubated with DOX-IO and DOX were examined as controls. The intracellular accumulation of DOX was examined by the fluorescent microscope utilizing the fluorescence of DOX. After 10 min incubation, fluorescence signal from DOX was observed in the nucleus only in the cells treated with free DOX, owing to the high permeability of the small molecules (i.e. DOX), which facilitated rapid influx into the nucleus. For the cells treated with DOX-IO and CN-DOX-IO, the fluorescence signal of DOX was localized mostly in the cytoplasm instead of the nucleus after 10 min incubation, implying the nanocarriers were uptake through the endocytic process. However, at 30 min after incubation, a small amount of DOX was observed to accumulate in the nucleus, which was ascribed to the slow release of DOX from DOX-IO and CN-DOX-IO. After 60 min incubation, DOX was evidenced in both cytoplasm and nucleus of the cells treated with DOX-IO and CN-DOX-IO, demonstrating that the sustained release of DOX from the nanoparticles enabled the continuous accumulation of DOX in the nucleus.

Uptake of CN-DOX-IO by Small Intestine Tissue Samples

To determine the uptake and permeability of CN-DOX-IO in the small intestine, the jejunum villi of the mouse small intestine was sectioned and incubated with CN-DOX-IO and DOX-IO, respectively, for 1 h. Prussian blue staining for iron revealed the distribution of CN-DOX-IO in the villi of the small intestine. Intense blue staining was observed in the sacs treated with CN-DOX-IO, in comparison with that of the DOX-IO treated samples. The results indicate that the casein outer layer may facilitate the interaction of nanoparticles with villi to increase the tissue uptake, subsequently enhancing the effective plasma concentration.

Distribution and Stability of CN-ICG-IO in Mice Observed with Optical/MR Imaging To study the stability and organ distribution profiles of the developed LBL drug delivery carriers in the GI tract in vivo, noninvasive NIR optical imaging was used to investigate mice fed with nanoparticles. CN-ICG-IO, in which DOX was substituted with indocyanine green (ICG), was orally administered to mice. ICG-IO was used as the control. Mouse stomach and intestine could be identified from the MR images. The accumulation of magnetic nanoparticles was confirmed by the change of MRI contrast, i.e., the almost complete loss of signal or darkening in the T2-weighted MR images, after oral administration of nanoparticles. At 3 h after oral administration, the NIR signal of ICG was found mostly in the intestine of the mice administered with CN-ICG-IO. However, the signal was mainly observed in the area of the stomach for the ICG-IO treated group, revealing the release of ICG from ICG-IO in the stomach. At 5 h after administration, NIR imaging showed that CN-ICG-IO reached into the ileum and spread further in the intestine. However, the NIR signal in the stomach was still highest in the animals treated with ICG-IO, while only a slight increase of NIR signal was observed in the small intestine. For the ICG-IO treated group, the signal in the stomach remained even up to 7 h, for the reason that the precipitation of ICG-IO formed and deposited in the crypts of gastric pits. The results from noninvasive NIR imaging thus further support that CN-ICG-IO could sustain in acidic gastric conditions, allowing for preferential delivery of the payload drugs to the small intestine. In addition, MRI contrast generated by iron oxide nanoparticles potentially enables the monitoring of drug delivery by MRI.

The invention claimed is:
1. A pharmaceutical composition comprising
a particle;
an inner coating on the particle comprising an amphiphilic polymer providing an space for embedding a hydrophobic drug within the inner coating, wherein a hydrophobic drug is in the space of the inner coating; and
an outer coating on the inner coating wherein the outer coating is crosslinked casein molecules.

2. The pharmaceutical composition of claim 1, wherein the particle is an iron oxide nanoparticle.

3. The pharmaceutical composition of claim 1, wherein the amphiphilic polymer comprises maleic acid and octadecene monomers.

4. The pharmaceutical composition of claim 1, wherein the hydrophobic drug is an anticancer drug.

5. The pharmaceutical composition of claim 4, wherein the anticancer drug is doxorubicin.

6. The pharmaceutical composition of claim 4, wherein the crosslinked casein molecules are made by the process of mixing casein and the particle comprising the inner coating in the presence of glutaraldehyde.

* * * * *